US00PP15552P2

(12) United States Plant Patent
Ballington

(10) Patent No.: US PP15,552 P2
(45) Date of Patent: Feb. 8, 2005

(54) STRAWBERRY PLANT NAMED 'BISH'

(50) Latin Name: *Fragaria×ananassa*
Varietal Denomination: Bish

(75) Inventor: James R. Ballington, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 10/685,163

(22) Filed: Oct. 14, 2003

(51) Int. Cl.[7] ..... A01H 5/00

(52) U.S. Cl. ..... Plt./208

(58) Field of Search ..... Plt./208

(56) References Cited

PUBLICATIONS

Declaration of James R. Ballington, Ph.D. under 37 C.F.R. Section 1.132; Jun. 14, 2004.

Release Announcement for Strawberry 'Bish,' Southeast Strawberry Expo; Nov. 7–8, 2002; Greenville, North Carolina.

*Primary Examiner*—Anne Marie Grunberg
*Assistant Examiner*—Annette H Para
(74) *Attorney, Agent, or Firm*—Myers Bigel Sibley & Sajovec, P.A.

(57) ABSTRACT

A new and distinct annual hill culture adapted variety of *Fragaria×ananassa* Duch. plant, designated 'Bish', is characterized by being significantly more resistant to anthracnose fruit rot than the current standard annual hill varieties 'Chandler' and 'Camarosa', while being equal to one or both these varieties for most other economically important fruit and plant characters. 'Bish' appears best adapted from the Southern Appalachians up through the Middle Atlantic regions of the United States.

2 Drawing Sheets

Latin name of the genus and species: The Latin name of the novel variety disclosed herein is *Fragaria×ananassa* Duch.

Variety Denomination: The inventive variety of strawberry disclosed herein has been given the variety denomination 'Bish'.

BACKGROUND OF THE INVENTION

The present invention relates to a new and distinct variety of Junebearing or short-day strawberry (*Fragaria×ananassa* Duch.), which has been named 'Bish'. This variety is the result of a cross between 'FL 87-210' (unpatented) and 'Delmarvel' (unpatented) made in 1993 in Raleigh, N.C. as part of a strawberry breeding program. Plants were first germinated in a greenhouse in Raleigh, N.C. in 1993. In the spring of 1994, germinated seedlings were transferred into seedling trays and allowed to grow over the summer. Subsequently, the seedlings were transplanted into the field in Reidsville, N.C. in the fall of 1994. 'Bish' was discovered in May 1995 in a cultivated field in Reidsville, N.C. and originally designated 'NCR 95-08' during the testing period.

'Bish' was first asexually reproduced by runners (i.e., stolons) and planted in Fletcher, N.C. in fall 1995. Subsequently, 'Bish' has also been asexually propagated by tissue culture micropropagation from runner meristems. The combination of traits disclosed herein that characterize 'Bish' have been retained true to type through successive cycles of asexual propagation.

SUMMARY OF THE INVENTION

'Bish' is a new and distinct variety of strawberry plant of the short-day type that is adapted to annual hill culture. It is significantly more resistant to anthracnose fruit rot than the current standard annual hill varieties 'Chandler' (U.S. Plant Pat. No. 5,262) and 'Camarosa' (U.S. Plant Pat. No. 8,708), while being equivalent to both of these varieties for most other economically important fruit and plant characteristics. Fruit skin color of 'Bish' is dark red and flesh color light red. The calyx is medium in size and reflexed. Petiole pubescence on 'Bish' is more dense than on 'Chandler', and basipetal in direction, compared with perpendicular to acropetal in the latter variety. 'Bish' is also characterized by the presence of two prominent leafy petiole bracts on mid-tier leaves.

DETAILED BOTANICAL DESCRIPTION OF THE VARIETY

Figure 1:
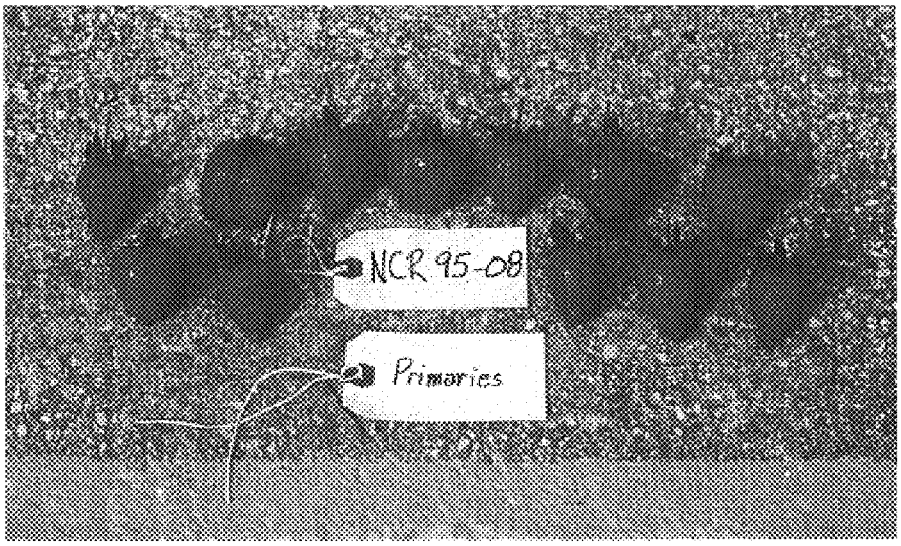
FIG. 1 shows fruit shape and color of 'Bish' strawberry.

The following is a detailed botanical description of a new and distinct variety of *Fragaria×ananassa* Duch. known as 'Bish'. The observations described below are from mature plants grown in test plots established in an annual hill strawberry production system on raised beds covered with black plastic mulch and subsurface drip irrigation.

Asexual propagules derived from the original source were established in an observation plot at Fletcher, N.C., in fall 1995, and in replicated trials at Reidsville and Fletcher, N.C., from 1996–2001; at Castle Hayne, N.C., in 1997 and 1999; and at Beltsville, Md., from 1998–2000. Plants were established in double offset rows spaced 12 inches apart on the beds with plants also spaced 12" apart within rows. The North Carolina test plots were established in a split plot design and the Beltsville plots in a randomized complete block design. All plots were established in late summer/early fall and data collected the following spring. Data from North Carolina locations in 1997–2003 and the Beltsville location from 1999–2001 are presented in Tables 1–30 below.

Those skilled in the art will appreciate that certain characteristics of the variety will vary with older or, conversely, with younger plants. 'Bish' has not been observed under all possible environmental conditions. Where dimensions, sizes, colors and other characteristics are given, it is to be understood that such characteristics are approximations or averages set forth as accurately as practicable. The phenotype of the variety may differ from the descriptions herein with variations in the environment such as season, temperature, light intensity, day length, cultural conditions, and the like. Color notations are based on The Royal Horticultural Society Colour Chart, The Royal Horticultural Society, London, 1995 edition.

'Bish' is a typical short-day strawberry variety with respect to seasonal growth cycle with a production pattern similar to 'Chandler', the most widely grown cultivar in annual hill strawberry culture in North Carolina at the present time. The five-plant observation plot of 'Bish' established at Fletcher, N.C., in fall 1995, yielded 1.04 kg of fruit per plant in 1996. On this basis, 'Bish' was chosen for further observation and testing, and was established in the first replicated trials in fall, 1996.

Technical Description of the Variety:

The performance of 'Bish' for yield and fruit size in replicated trials in North Carolina is summarized in Tables 1–14 below. Performance at Beltsville, Md., is summarized in Table 15. Fruit quality characteristics are summarized in Tables 16–26. Technical descriptive data are included in Tables 27–30.

In addition to overall performance on a site, planting date was also a variable, since ideal planting date varies by location and often also varies among varieties. In 2001 and 2002, "original" (OR) source plants of 'Bish' were also compared to meristemmed and virus-tested source plants. In the tables and description below, the latter are referred to as: (99) tissue-culture propagated in 1999; (00) tissue-culture (TC) propagated in 2000; and (MD) remeristemmed and virus-tested by the Maryland Department of Agriculture.

Yield and Fruit Size (weight): The performance of 'Bish' for yield and fruit size in replicated trials in North Carolina is summarized in Tables 1–14 below. Table 1 provides the performance of 'Bish' in annual hill culture at the Upper Piedmont Research Station, Reidsville, N.C. in 1997. The yield and size were based on four, five-plant plots each across two planting dates.

TABLE 1

| | Planting Date | | | |
|---|---|---|---|---|
| | Sep. 17, 1996 | | Sep. 24, 1996 | |
| Selection | Marketable Yield (g/plant) | Size (g/berry) | Marketable Yield (g/plant) | Size (g/berry) |
| 'Bish' | 136* | 17.1A | 235* | 16.0* |
| 'Camarosa' | 189* | 22.2A | 161* | 20.0* |
| 'Chandler' | 151* | 17.1A | 180* | 18.0* |
| 'Delmarvel'[1] | 181* | 14.7B | 91* | 17.0* |
| 'NCS 93-05'[2] | 143* | 20.5A | 177* | 20.8* |

[1,2]Unpatented
*Indicates no significant differences observed.
Mean separation was by a Duncan's Multiple Range Test with $p \leqq 0.05$ and values designated with different letters are statistically different.

Table 2 discloses the performance of 'Bish' in annual hill culture at the Mountain Horticultural Crops Research Station, Fletcher, N.C. in 1997. The marketable yield and size were based on four, five-plant plots across two planting dates.

TABLE 2

| | Planting Date | | | | |
|---|---|---|---|---|---|
| | Aug. 15, 1996 | | Aug. 22, 1996 | | |
| Selection | Market. Yield (g/plant) | Size (g/berry) | Market. Yield (g/plant) | Size (g/berry) | % Athracnose[1] |
| 'Bish' | 551* | 15.2B | 675A | 17.0B | 0.0 |
| 'Apollo'[2] | 609* | 15.3B | 585ABC | 16.0B | 0.5 |
| 'Chandler' | 597* | 14.9B | 652AB | 16.3B | 5.0 |
| 'Jewel'[3] | 536* | 12.2B | 499ABC | 15.3B | 3.4 |
| 'NCS 93-05' | 521* | 24.5A | 447BC | 26.8A | 0.6 |

[1]Percent by weight of fruit infected by strawberry anthracnose caused by *Colletotrichum acutatum*.
[2]Unpatented
[3]United States PP5,897
*Indicates no significant differences observed.
Mean separation was by a Duncan's Multiple Range Test with $p \leqq 0.05$ and values designated with different letters are statistically different.

Table 3 provides the performance of 'Bish' in annual hill culture at the Horticultural Crops Research Station, Castle Hayne, N.C. in 1998. The yield and size were based on four, 10-plant replicates planted Oct. 15, 1997.

TABLE 3

| Selection | Marketable Yield (g/plant) | Fruit Size (g/plant) | % Athracnose[1] |
|---|---|---|---|
| 'Bish' | 210A | 17C | 4.8A |
| 'Camarosa' | 201A | 22B | 38.4C |
| 'Chandler' | 35B | 18C | 42.7C |
| 'NCS 93-05' | 86B | 25A | 23.6B |

[1]Percent by weight of fruit infected by strawberry anthracnose caused by *Colletotrichum acutatum*.
Mean separation was by a Duncan's Multiple Range Test with $p \leqq 0.05$ and values designated with different letters are statistically different.

Table 4 provides the performance of 'Bish' in annual hill culture at the Upper Piedmont Research Station, Reidsville, N.C. in 1998. The yield and size were based on four, 10-plant replicates planted Sep. 15, 1997.

TABLE 4

| Selection | Marketable Yield (g/plant) | Fruit Size (g/plant) | % Athracnose[1] |
|---|---|---|---|
| 'Bish' | 219A | 14.7B | 2.3A |
| 'Chandler' | 190A | 13.9B | 22.3C |
| 'NCS 93-05' | 132B | 20.1A | 11.3B |

[1]Percent by weight of fruit infected by strawberry anthracnose caused by *Colletotrichum acutatum*.
Mean separation was by a Duncan's Multiple Range Test with $p \leqq 0.05$ and values designated with different letters are statistically different.

Table 5 provides the performance of 'Bish' in annual hill culture in Fletcher, N.C. in 1998. The yield and size were based on four, 10-plant replicates planted Aug. 15, 1997.

TABLE 5

| Selection | Marketable Yield (g/plant) | Fruit Size (g/plant) | % Athracnose[1] |
|---|---|---|---|
| 'Bish' | 385A | 14.9* | 0.04A |
| 'Chandler' | 327B | 14.2* | 34.0C |
| 'NCS 93-05' | 274C | 18.1* | 12.6B |

[1]Percent by weight of fruit infected by strawberry anthracnose caused by *Colletotrichum acutatum*.
*Indicates no significant differences observed.
Mean separation was by a Duncan's Multiple Range Test with p ≦ 0.05 and values designated with different letters are statistically different.

Table 6 provides the performance of 'Bish' in annual hill culture at the Upper Piedmont Research Station, Reidsville, N.C. in 1999. The yield and size were based on three, 10-plant replicates for each of the three planting dates.

TABLE 6

| | Planting Date | | | | | |
|---|---|---|---|---|---|---|
| | Sep. 10, 1998 | | | Sep. 17. 1998 | | |
| Selection | Mkt. Yld.[1] | Size[2] | % Anth.[3] | Mkt. Yld.[1] | Size[2] | % Anth.[3] |
| 'Bish' | 277B | 12.7C | 0.0A | 207C | 12.3B | 0.0A |
| 'Camarosa' | 316A | 14.4B | 4.0B | 400A | 17.5A | 1.0B |
| 'Chandler' | 308AB | 12.8C | 4.2B | 281B | 12.2B | 1.8B |
| 'NCS 93-05' | 168C | 17.5A | 0.0A | 211C | 17.9A | 0.0A |

| | Planting Date Sep. 23, 1998 | | |
|---|---|---|---|
| Selection | Mkt Yld.[1] | Size[2] | % Anth.3 |
| 'Bish' | 246B | 13.5B | 0.3B |
| 'Camarosa' | 281A | 15.9A | 0.0A |
| 'Chandler' | 230B | 12.6B | 0.7C |
| 'NCS 93-05' | 149C | 17.9A | 0.0A |

[1]Mkt. Yld. is marketable yield expressed as g/plant.
[2]Size is expressed as g/berry.
[3]% Anth. is percent by weight of fruit infected by strawberry anthracnose caused by *Colletotrichum acutatum*.
Mean separation was by a Duncan's Multiple Range Test with p ≦ 0.05 and values designated with different letters are statistically different.

Table 7 provides the performance of 'Bish' in annual hill culture at Fletcher, N.C. in 1999. The yield and size were based on three, 10-plant replicates for each of the three planting dates.

TABLE 7

| | Planting Date | | | | | |
|---|---|---|---|---|---|---|
| | Aug. 17, 1998 | | | Aug. 24, 1998 | | |
| Selection | Mkt. Yld.[1] | Size[2] | % Anth.[3] | Mkt. Yld.[1] | Size[2] | % Anth.[3] |
| 'Bish' | 580A | 15C | 0.1A | 562A | 15C | 0.1A |
| 'Camarosa' | 445B | 18B | 30B | 378B | 18B | 34C |
| 'Chandler' | 88C | 14D | 50C | 498B | 14D | 6B |
| 'NCS 93-05' | 547AB | 21A | 2.6A | 413C | 22A | 0.1A |

TABLE 7-continued

| | Planting Date Aug. 31, 1998 | | |
|---|---|---|---|
| Selection | Mkt. Yld.[1] | Size[2] | % Anth.[3] |
| 'Bish' | 622A | 16B | 0.1A |
| 'Camarosa' | — | — | — |
| 'Chandler' | 467B | 13C | 13B |
| 'NCS 93-05' | 408C | 21A | 0.1A |

[1]Mkt. Yld. is marketable yield expressed as g/plant.
[2]Size is expressed as g/berry.
[3]% Anth. is percent by weight of fruit infected by stawberry anthracnose caused by *Colletotrichum acutatum*.
Mean separation was by a Duncan's Multiple Range Test with p ≦ 0.05 and values designated with different letters are statistically different.

Table 8 provides the performance of 'Bish' in annual hill culture at Castle Hayne, N.C. in 2000. The yield, size, and % anthracnose values were averages of three, 20-plant plots on each of three planting dates.

TABLE 8

| | Planting Date | | | | | |
|---|---|---|---|---|---|---|
| | Oct. 14, 1999 | | | Oct. 20, 1999 | | |
| Selection | Mkt. Yld.[1] | Size[2] | % Anth.[3] | Mkt. Yld.[1] | Size[2] | % Anth.[3] |
| 'Bish' | 333A | 13B | 0 | 200A | 19C | 1.1B |
| 'Camarosa' | — | — | — | 132BC | 22BC | 41.9D |
| 'Chandler' | 174C | 18A | 0 | 80D | 21BC | 51.4E |
| 'Gaviota'[4] | — | — | — | 199A | 23AB | 2.2B |
| 'Gem Star'[5] | — | — | — | 113C | 27A | 33.0C |
| 'Sw Charlie'[6] | 216B | 16A | 0 | 152B | 19C | 0.0A |

| | Planting Date Oct. 27, 1999 | | |
|---|---|---|---|
| Selection | Mkt. Yld.[1] | Size[2] | % Anth.[3] |
| 'Bish' | 205A | 18B | 0.0A |
| 'Camarosa' | 42D | 22AB | 50.6E |
| 'Chandler' | 177BC | 19AB | 35.6D |
| 'Gaviota'[4] | 188AB | 23A | 3.9B |
| 'Gem Star'[5] | 181BC | 23A | 19.0C |
| 'Sw Charlie'[6] | 163C | 20AB | 0.0A |

[1]Mkt. Yld. is marketable yield expressed as g/plant.
[2]Size is expressed as g/berry.
[3]% Anth. is percent by weight of fruit infected by stawberry anthracnose caused by *Colletotrichum acutatum*.
[4]United States PP10,461
[5]United States PP12,377
[6]United States PP8,729
Mean separation was by a Duncan's Multipie Range Test with p ≦ 0.05 and values designated with different letters are statistically different.

Table 9 discloses the performance of 'Bish' in annual hill culture in Reidsville, N.C. in 2000. The yield and size were based on three, 10-plant replicates each on each planting date.

TABLE 9

| | Planting Date | | | | | |
|---|---|---|---|---|---|---|
| | Sep. 15, 1999 | | | Sep. 22, 1999 | | |
| Selection | Marketable Yield (g/plant) | Size (g/berry) | % Anthracnose[1] | Marketable Yield (g/plant) | Size (g/berry) | % Anthracnose[1] |
| 'Bish' | 327A | 17B | 0A | 209AB | 14C | 0A |
| 'Camarosa' | 303A | 20B | 26C | 147B | 17BC | 12C |

TABLE 9-continued

| | Planting Date | | | | | |
|---|---|---|---|---|---|---|
| | Sep. 15, 1999 | | | Sep. 22, 1999 | | |
| Selection | Marketable Yield (g/plant) | Size (g/berry) | % Anthracnose[1] | Marketable Yield (g/plant) | Size (g/berry) | % Anthracnose[1] |
| 'Chandler' | 257AB | 17B | 6B | 241A | 19B | 10C |
| 'Gaviota' | 135C | 21AB | 3B | 145B | 21AB | 0A |
| 'Gem Star' | 216B | 24A | 11BC | 232A | 24A | 5B |

[1]Percent by weight of fruit infected by strawberry antracnose caused by *Colletotrichum acutatum*.
Mean separation was by a Duncan's Multiple Range Test with $p \leqq 0.05$ and values designated with different letters are statistically different.

Table 10 provides the performance of 'Bish' in annual hill culture at Fletcher, N.C. in 2000. The yield, size, and % anthracnose values were averages of three, 20-plant plots on each of the three planting dates.

TABLE 10

| | Planting Date | | | | | |
|---|---|---|---|---|---|---|
| | Aug. 4, 1999 | | | Aug. 11, 1999 | | |
| Selection | Mkt. Yld.[1] | Size[2] | % Anth.[3] | Mkt. Yld.[1] | Size[2] | % Anth.[3] |
| 'Bish' | 701B | 16* | 0.1A | 639B | 15B | 0.1A |
| 'Chandler' | 781A | 16* | 0.5B | 758A | 16A | 0.2B |
| 'Gaviota' | — | — | — | — | — | — |
| 'Gem Star' | — | — | — | — | — | — |

| | Planting Date Aug. 18, 1999 | | |
|---|---|---|---|
| Selection | Mkt. Yld.[1] | Size[2] | % Anth.[3] |
| 'Bish' | 585B | 16BC | 0.1A |
| 'Chandler' | 705A | 15C | 0.8B |
| 'Gaviota' | 308D | 17B | 0.2A |
| 'Gem Star' | 543C | 22A | 2.0C |

[1]Mkt. Yld. is marketable yield expressed as g/plant.
[2]Size is expressed as g/berry.
[3]% Anth. is percent by weight of fruit infected by strawberry anthracnose caused by *Colletotrichum acutatum*.
*Indicates no significant differences observed.
Mean separation was by a Duncan's Multiple Range Test with $p \leqq 0.05$ and values designated with different letters are statistically different.

Table 11 provides the performance of 'Bish' in annual hill culture at the Upper Piedmont Research Station, Reidsville, N.C. in 2001. The yield was reduced due to a cool fall resulting in reduced daughter crown development. The yield and size were based on three replicates of 10 plants each on each planting date.

TABLE 11

| | Planting Date | | | |
|---|---|---|---|---|
| | Sep. 22, 2000 | | Sep. 29, 2000 | |
| Selection | Marketable Yield (g/plant) | Size (g/berry) | Marketable Yield (g/plant) | Size (g/berry) |
| 'Bish'(Original) | 154B | 20* | 93B | 16B |
| 'Bish'(99-TC) | 201A | 17* | 96B | 18A |

TABLE 11-continued

| | Planting Date | | | |
|---|---|---|---|---|
| | Sep. 22, 2000 | | Sep. 29, 2000 | |
| Selection | Marketable Yield (g/plant) | Size (g/berry) | Marketable Yield (g/plant) | Size (g/berry) |
| 'Bish'(00-TC) | 125B | 18* | — | — |
| 'Camarosa' | 231A | 21* | 118AB | 20A |
| 'Chandler' | 208A | 18* | 146A | 19A |

*Indicates no significant differences observed.
Mean separation was by a Duncan's Multiple Range Test with $p \leqq 0.05$ and values designated with different letters are statistically different.

Table 12 discloses the performance of 'Bish' in annual hill culture in Fletcher, N.C. in 2001. The yield was reduced due to a cool fall resulting in reduced daughter crown development. The yield and size were based on three, 10-plant replicates for each planting date.

TABLE 12

| | Planting Date | | | |
|---|---|---|---|---|
| | Aug. 23, 2000 | | Aug. 30, 2000 | |
| Selection | Marketable Yield (g/plant) | Size (g/berry) | Marketable Yield (g/plant) | Size (g/berry) |
| 'Bish'(Original) | 330C | 16C | 420B | 16B |
| 'Bish'(99-TC) | 420B | 16C | 392B | 18AB |
| 'Bish'(00-TC) | 391B | 16C | 357BC | 15BC |
| 'Camarosa' | 537A | 18AB | 408B | 19AB |
| 'Chandler' | 540A | 18AB | 542A | 17B |
| 'NCS 93-05' | 255D | 20A | 231D | 22A |

Mean separation was by a Duncan's Multiple Range Test with $p \leqq 0.05$.

Table 13 provides the performance of 'Bish' in annual hill culture at the Upper Piedmont Research Station, Reidsville, N.C. in 2002. The yield and size were averaged across three, 10-plant replicates for each of two planting dates (Sep. 5, 2001 and Sep. 12, 2001).

TABLE 13

| Selection | Marketable Yield (g/plant) | Fruit Size (g/plant) | % Anthracnose[1] |
|---|---|---|---|
| 'Bish'(Original) | 231* | 14.2AB | 0.0A |
| 'Bish'(99-TC) | 260* | 12.8BC | 0.0A |
| 'Bish'(00-TC) | 257* | 13.2BC | 0.0A |
| 'Camarosa' | 446* | 15.1A | 3.5C |
| 'Chandler' | 440* | 11.4D | 0.3B |

[1]Percent by weight of fruit infected by strawberry anthracnose caused by *Colletotrichum acutatum*.
*Indicates no significant differences observed.
Mean separation was by a Duncan's Multiple Range Test with $p \leqq 0.05$ and values designated with different letters are statistically different.

Table 14 discloses the performance of 'Bish' in annual hill culture in Fletcher, N.C. in 2002. The yield, size and % anthracnose were based on three, 10-plant replicates each on each planting date.

TABLE 14

| Selection | Planting Date: Aug. 15, 2001 Marketable Yield (g/plant) | Size (g/berry) | % Anthracnose[1] | Aug. 22, 2001 Marketable Yield (g/plant) | Size (g/berry) | % Anthracnose[1] |
|---|---|---|---|---|---|---|
| 'Bish'(OR) | 455B | 12D | 0.0A | 390C | 13B | 0.0A |
| 'Bish'(MD) | 382C | 13C | 0.0A | 488B | 12BC | 0.0A |
| 'Camarosa' | 467B | 14C | 0.1B | 520AB | 14B | 0.0A |
| 'Chandler' | 512A | 15B | 0.0A | 548A | 13B | 0.1B |
| 'Gem Star' | 461B | 17A | 2.2C | 559A | 18A | 0.4C |

[1]Percent by weight of fruit infected by strawberry antracnose caused by *Colletotrichum acutatum*.
Mean separation was by a Duncan's Multiple Range Test with p ≦ 0.05 and values designated with different letters are statistically different.

The performance of 'Bish' in annual hill culture at Beltsville, Md. between 1999 and 2001 is summarized in Table 15. 'Bish' was an outstanding performer in replicated trials at Beltsville, Md. The yield and size were based on results from replicated trials involving four, five-plant plots on raised beds with plastic mulch and drip irrigation, but without preplant fumigation.

TABLE 15

| Selection | 1999 Yield/plant (g/plant) | 1999 Size (g/berry) | 2000 Yield/plant (g/plant) | 2000 Size (g/berry) | 2001[1] Yield/plant (g/plant) | 2001[1] Size (g/berry) |
|---|---|---|---|---|---|---|
| 'Bish' | 750A | 13.7BC | 620* | 13.4* | 530AB | 14.2B |
| 'Allstar'[2] | 880A | 13.5BC | 700* | 13.9* | 680A | 14.9B |
| 'Chandler' | 720AB | 11.7C | 550* | 12.8* | 480AB | 15.5B |
| 'Northeaster'[3] | 790A | 13.1C | 580* | 15.0* | 450ABC | 17.2AB |
| 'NCS 93-05' | 520B | 16.3A | — | — | 250C | 20.1A |

[1]Yields were reduced due to a cool fall, resulting in reduced daughter crown development.
[2,3]Unpatented
*Indicates no significant differences observed.
Mean separation was by a Duncan's Multiple Range Test with p ≦ 0.05 and values designated with different letters are statistically different.

Overall, 'Bish' was generally equivalent to 'Chandler' for yield and fruit size in North Carolina plots. This same pattern was observed when compared with 'Camarosa' for yield. However, 'Camarosa' typically produced larger fruit than 'Bish'. Yields across locations in North Carolina were generally higher at Fletcher; the plant also appeared to be well-adapted at Beltsville, Md. Therefore, the preferred region of adaptation for 'Bish' appears to be the Southern Appalachians up through the Middle Atlantic States. A consistent pattern for yield differences by planting date was not observed. Thus, it is contemplated that planting dates suitable for 'Chandler' will also be suitable for 'Bish'. Further, there was no consistent differences among plant sources, i.e., original vs. 99 vs. 00 vs. MD (see Tables 11–14). Accordingly, 'Bish' is genetically stable when propagated by micropropagation.

Fruit Characteristics: The performance of 'Bish' for fruit appearance (attractiveness), firmness, symmetry (shape and uniformity), skin toughness (resistance to abrasion) and flavor in subjective evaluations is summarized in Tables 16–26. The values provided in Tables 16–26 were based on a subjective 0–90 scale where less than 60 was unacceptable, 60–69 was acceptable, 70–79 was good, and 80 and above was superior.

Table 16 discloses fruit characteristics of 'Bish' grown at the Horticultural Crops Research Station, Castle Hayne, N.C. in 1998. The averages were of ratings across four, 10-plant plots with separation by Duncan's Multiple Range Test with p≦0.05.

TABLE 16

| Selection | Appearance | Firmness | Symmetry | Skin Color | Flesh Color | Skin Toughness | Flavor |
|---|---|---|---|---|---|---|---|
| 'Bish' | 77AB | 77BC | 76* | 77* | 73B | 77B | 76B |
| 'Camarosa' | 77AB | 81A | 75* | 78* | 76A | 81A | 71C |
| 'Chandler' | 75B | 76C | 75* | 77* | 77A | 77B | 76B |
| 'NCS 93-05' | 79A | 79AB | 76* | 79* | 79A | 78AB | 79A |

*Indicates no significant differences observed.
Values designated with different letters are statistically different.

Table 17 shows fruit characteristics of 'Bish' grown at the Upper Piedmont Research Station, Reidsville, N.C. in 1998. The averages were of ratings across four, 10-plant plots with separation by Duncan's Multiple Range Test with p≦0.05.

TABLE 17

| Selection | Appearance | Firmness | Symmetry | Skin Color | Flesh Color | Skin Toughness | Flavor |
|---|---|---|---|---|---|---|---|
| 'Bish' | 74B | 74* | 74B | 74B | 73* | 72.5B | 75.0B |
| 'Chandler' | 75B | 75* | 75AB | 75A | 75* | 75.0A | 75.0B |
| 'NCS 93-05' | 78A | 74* | 77A | 78A | 75* | 72.5B | 77.5A |

*Indicates no significant differences observed.
Values designated with different letters are statistically different.

Table 18 discloses fruit characteristics of 'Bish' grown at the Mountain Horticultural Crops Research Station, Fletcher, N.C. in 1998. The averages were of ratings across four, 10-plant plots with separation by Duncan's Multiple Range Test with p≦0.05.

TABLE 18

| Selection | Appearance | Firmness | Symmetry | Skin Color | Flesh Color | Skin Toughness | Flavor |
|---|---|---|---|---|---|---|---|
| 'Bish' | 78* | 79* | 78* | 79* | 71B | 76* | 76* |
| 'Chandler' | 75* | 76* | 74* | 76* | 76A | 76* | 72* |
| 'NCS 93-05' | 75* | 81* | 75* | 79* | 76A | 80* | 75* |

*Indicates no significant differences observed.
Values designated with different letters are statistically different.

Table 19 discloses fruit characteristics of 'Bish' grown at the Upper Piedmont Research station, Reidsville, N.C. in 1999. Values were of averages of three replicates for a September 17 planting date with mean separation by Duncan's Multiple Range Test with p≦0.05.

TABLE 19

| Selection | Appearance | Firmness | Symmetry | Skin Color | Flesh Color | Skin Toughness | Flavor |
|---|---|---|---|---|---|---|---|
| 'Bish' | 76.3AB | 80.8B | 75.0AB | 79.3* | 72.5C | 80.0B | 77.1A |
| 'Camarosa' | 75.2B | 85.5A | 73.3B | 78.8* | 78.2A | 84.3A | 68.7B |
| 'Chandler' | 71.7C | 77.5C | 70.0C | 80.0* | 75.0BC | 76.7C | 76.3A |

TABLE 19-continued

| Selection | Appearance | Firmness | Symmetry | Skin Color | Flesh Color | Skin Toughness | Flavor |
|---|---|---|---|---|---|---|---|
| 'NCS 93-05' | 78.3A | 80.8B | 76.5A | 79.2* | 75.3B | 80.5B | 75.3A |

*Indicates no significant differences observed.
Values designated with different letters are statistically different.

Table 20 discloses fruit characteristics of 'Bish' grown at Fletcher, N.C. in 1999. Values were of averages of three replicates across each of three planting dates (Aug. 17, 1998; Aug. 24, 1998; and Aug. 30, 1998) with mean separation by Duncan's Multiple Range Test with $p \leqq 0.05$.

TABLE 20

| Selection | Appearance | Firmness | Symmetry | Skin Color | Flesh Color | Skin Toughness | Flavor |
|---|---|---|---|---|---|---|---|
| 'Bish' | 77B | 80B | 77A | 79* | 72B | 80B | 79A |
| 'Camarosa' | 74C | 84A | 73B | 79* | 74A | 83A | 69C |
| 'Chandler' | 71D | 77C | 71C | 79* | 75A | 77C | 75B |
| 'NCS 93-05' | 80A | 80B | 79A | 80* | 74A | 80B | 78A |

*Indicates no significant differences observed.
Values designated with different letters are statistically different.

Table 21 provides fruit characteristics of 'Bish' grown at Castle Hayne, N.C. in 2000. Values were of averages of four, 20-plant plots with mean separation by Duncan's Multiple Range Test with $p \leqq 0.05$.

TABLE 21

| Selection | Appearance | Firmness | Symmetry | Skin Color | Flesh Color | Skin Toughness | Flavor |
|---|---|---|---|---|---|---|---|
| 'Bish' | 75B | 76B | 76A | 78A | 74B | 74CD | 75A |
| 'Camarosa' | 74B | 80A | 74B | 76AB | 76A | 80A | 72BC |
| 'Chandler' | 69C | 75B | 72C | 75BC | 76A | 75C | 74AB |
| 'Gaviota' | 76A | 76B | 75A | 78A | 76A | 72E | 75A |
| 'Sw. Charlie' | 76A | 73C | 74B | 74C | 70C | 73DE | 71C |
| 'NCC 87-45' | 70C | 75B | 74B | 69D | 69C | 76B | 71C |

[1]Unpatented
Values designated with different letters are statistically different.

Table 22 provides fruit characteristics of 'Bish' grown at Reidsville, N.C. in 2000. Values were of averages of three replicates of a Sep. 5, 1999 planting date with mean separation by Duncan's Multiple Range Test with $p \leqq 0.05$.

TABLE 22

| Selection | Appearance | Firmness | Symmetry | Skin Color | Flesh Color | Skin Toughness | Flavor |
|---|---|---|---|---|---|---|---|
| 'Bish' | 76AB | 76B | 76A | 79A | 77AB | 74B | 78A |
| 'Camarosa' | 72C | 80A | 73B | 78A | 78A | 80A | 75B |
| 'Chandler' | 72C | 75B | 73B | 76B | 75B | 75B | 75B |
| 'Gaviota' | 78A | 75B | 75AB | 80A | 76AB | 75B | 75B |
| 'Gem Star' | 75BC | 75B | 75AB | 75B | 70C | 75B | 75B |

Values designated with different letters are statistically different.

Table 23 provides fruit characteristics of 'Bish' grown at Fletcher, N.C. in 2000. Values were of averages of three, 20-plant replicates of an Aug. 18, 1999 planting date with mean separation by Duncan's Multiple Range Test with $p \leqq 0.05$.

TABLE 23

| Selection | Appearance | Firmness | Symmetry | Skin Color | Flesh Color | Skin Toughness | Flavor |
|---|---|---|---|---|---|---|---|
| 'Bish' | 76B | 79A | 75B | 80A | 72* | 78A | 73AB |
| 'Chandler' | 70D | 70B | 70C | 75B | 75* | 70B | 73AB |
| 'Gaviota' | 80A | 80A | 80A | 80A | 73* | 78A | 75A |
| 'Gem Star' | 73C | 78A | 75B | 72C | 70* | 78A | 70B |

*Indicates no significant differences observed.
Values designated with different letters are statistically different.

Table 24 provides fruit characteristics of 'Bish' grown at Fletcher, N.C. in 2001. Values were of averages of three replicates of two planting dates (Aug. 14, 2000 and Aug. 22, 2000) with mean separation by Duncan's Multiple Range Test with $p \leqq 0.05$.

TABLE 24

| Selection | Appearance | Firmness | Symmetry | Skin Color | Flesh Color | Skin Toughness | Flavor |
|---|---|---|---|---|---|---|---|
| 'Bish' (original) | 73AB | 75* | 73A | 72* | 73* | 75A | 70* |
| 'Bish' (99-TC) | 70B | 75* | 72AB | 72* | 75* | 70B | 72* |
| 'Bish' (00-TC) | 75A | 75* | 73A | 73* | 75* | 75A | 72* |
| 'Camarosa' | 75A | 75* | 70B | 72* | 77* | 75A | 70* |
| 'Chandler' | 73AB | 75* | 72AB | 75* | 77* | 73AB | 68* |
| 'NCS 93-05' | 75A | 75* | 73A | 72* | 77* | 75A | 75* |

*Indicates no significant differences observed.
Values designated with different letters are statistically different.

Table 25 provides fruit characteristics of 'Bish' grown at the Upper Peidmont Research Station, Reidsville, N.C. in 2002. Values were of averages across Sep. 5, 2001 and Sep. 12, 2001 planting dates with mean separation by Duncan's Multiple Range Test with $p \leqq 0.05$.

TABLE 25

| Selection | Appearance | Firmness | Symmetry | Skin Color | Flesh Color | Skin Toughness | Flavor |
|---|---|---|---|---|---|---|---|
| 'Bish' (original) | 77A | 77B | 75A | 77A | 71B | 78B | 79A |
| 'Bish' (99-TC) | 77A | 78B | 75A | 77A | 71B | 78B | 78A |
| 'Bish' (00-TC) | 75A | 77B | 74A | 77A | 71B | 78B | 77A |
| 'Camarosa' | 72B | 84A | 71B | 76AB | 77A | 82A | 71C |
| 'Chandler' | 70B | 75C | 70B | 75B | 75A | 74C | 74B |

Values designated with different letters are statistically different.

Table 26 provides fruit characteristics of 'Bish' grown at Fletcher, N.C. in 2002. Values were of averages across Aug. 15, 2001 and Aug. 22, 2001 planting dates with mean separation by Duncan's Multiple Range Test with $p \leqq 0.05$.

TABLE 26

| Selection | Appearance | Firmness | Symmetry | Skin Color | Flesh Color | Skin Toughness | Flavor |
|---|---|---|---|---|---|---|---|
| 'Bish' (OR) | 78A | 76B | 75A | 80A | 72A | 77BC | 77A |
| 'Bish' (MD) | 77A | 77B | 75A | 80A | 72A | 78BC | 78A |
| 'Camarosa' | 73B | 80A | 70BC | 78AB | 74A | 85A | 68C |
| 'Chandler' | 72B | 72C | 70BC | 78AB | 74A | 75C | 74AB |
| 'Gem Star' | 75AB | 76B | 72AB | 70C | 64B | 79B | 72C |

Values designated with different letters are statistically different.

Figure 2:
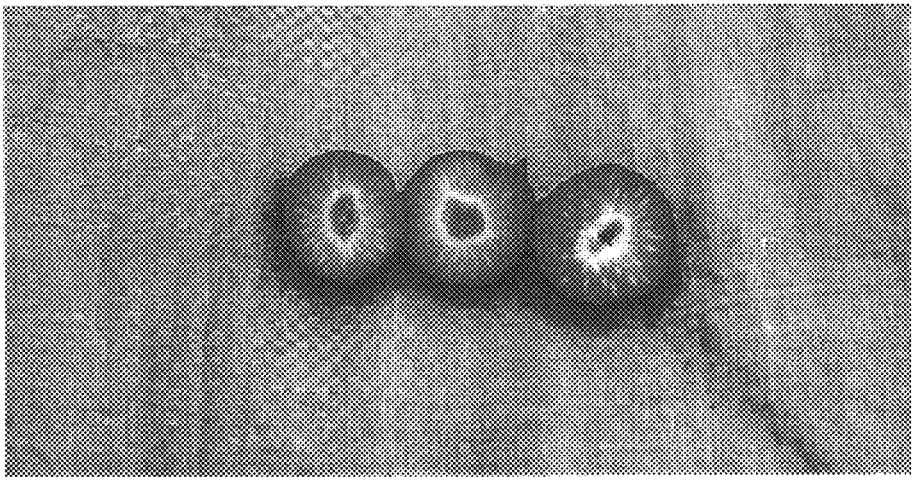
FIG. 2 shows internal flesh color of 'Bish' strawberry.

'Bish' was equal to or better than 'Chandler' for fruit appearance, firmness, symmetry, skin toughness and flavor. Further, 'Bish' was superior to 'Camarosa' for flavor, and equal to or better than 'Camarosa' for appearance and symmetry. 'Camarosa' fruit are extremely firm and also have excellent skin toughness. 'Bish' fruit were neither as firm nor as tough as 'Camarosa', but were satisfactory for both of these traits. In these subjective evaluations 'Bish' was equal to both 'Chandler' and 'Camarosa' for skin color, and poorer than these varieties for flesh color, but still satisfactory for the latter trait. The skin of 'Bish' was uniformly glossy and dark red, but slightly uneven in color (FIG. 1). The skin color on the lighter side of the fruit matches Royal Horticultural Society (RHS) color chip 53A, and the darker side chip 187A. Flesh color of 'Bish' fruit matches RHS color chip 33A, and the central vascular cylinder was whitish (FIG. 2). Hollow centers occur in 80% of the berries. Where these occur, the mean diameter is 5 mm. The range is from 2–10(14) mm (observed May 2004 in Raleigh, N.C.). The achenes on the surface were yellow and slightly indented (sunken), so that the outer surface of the achene is even with the surface of the receptacle tissue between the achenes. As observed in May 2004, in Raleigh, N.C., the color of the achenes on the exposed side of the fruit is RHS color chip 53A to 53B. Achenes on the side away from the sun correspond to R.H.S. color chip 1C in color.

Subjective observations indicate that the shape of the fruit of 'Bish' ranges primarily from blunt conic (with some primary fruit) to conic (FIG. 1). The calyx is medium in size and reflexed (FIG. 1). Fruit shape of 'Bish' was more uniform than 'Chandler' across primary, secondary, and higher order fruits (Table 27).

TABLE 27

| Selection | | Length/Width Ratio | | |
|---|---|---|---|---|
| | | Primary | Secondary | Tertiary, etc. |
| 'Chandler' | Mean | 1.22 | 1.12 | 1.29 |
| | Range | 1.00–1.44 | 1.00–1.39 | 1.00–1.63 |
| 'Bish' | Mean | 1.19 | 1.18 | 1.19 |
| | Range | 1.00–1.34 | 1.05–1.24 | 1.07–1.41 |

Fruit shape characteristics were from plants grown in Fletcher, NC in 2002.

Flowers and Flowering Characteristics: Both primary and secondary flowers of 'Bish' were slightly larger than 'Chandler' (Table 28).

TABLE 28

| Selection | | Calyx Diameter (mm) | | Corolla | Sepal |
|---|---|---|---|---|---|
| | | Outer | Inner | Diameter (mm) | Number |
| 'Chandler' | Primary | | | | |
| | Mean | 30 | 31 | 31 | 13 |
| | Range | 27–34 | 28–34 | 27–35 | 13–14 |
| | Secondary | | | | |
| | Mean | 25 | 27 | 30 | 13 |
| | Range | 23–27 | 24–29 | 28–32 | 11–15 |
| 'Bish' | Primary | | | | |
| | Mean | 32 | 34 | 34 | 11 |
| | Range | 30–35 | 31–40 | 31–40 | 10–12 |
| | Secondary | | | | |
| | Mean | 28 | 30 | 31 | 11 |
| | Range | 25–30 | 28–32 | 30–33 | 10–12 |

TABLE 28-continued

| Selection | | Petal Number | Petal Length (mm) | Petal Width (mm) |
|---|---|---|---|---|
| 'Chandler' | Primary | | | |
| | Mean | 7 | 12 | 12 |
| | Range | 6–7 | 9–14 | 8–13 |
| | Secondary | | | |
| | Mean | 6 | 10 | 11 |
| | Range | 5–7 | 9–13 | 9–13 |
| 'Bish' | Primary | | | |
| | Mean | 6 | 13 | 11 |
| | Range | 5–6 | 8–16 | 7–14 |
| | Secondary | | | |
| | Mean | 5 | 12 | 11 |
| | Range | 5–6 | 9–14 | 8–12 |

Flower measurements were from plants grown in Reidsville, NC in 2003.

For both 'Bish' and 'Chandler', the diameter of the outer calyx of primary flowers is generally equal to that of the corolla, and slightly smaller than the corolla on secondary flowers. The basal half of the calyx is fused (calyx tube) and adherent to the fruit. The apical half of the calyx lobes are free and typically range from clasping to perpendicular to slightly reflexed in pose on each fruit. The calyx is inserted beneath the fruit, with the calyx tube forming a concave indention in the base of the fruit. Sepal number averaged 11 for 'Bish' and 13 for 'Chandler'. Mean petal number was also slightly less on both primary and secondary petals for 'Bish'. Petal length for 'Bish' was somewhat greater than width, while for 'Chandler' they were essentially the same. The petal color of flowers produced by 'Bish' is white, corresponding closest to RHS color chip 155C, however the petals are whiter than RHS 155C or any of the other RHS color chips. The average date of first flowering for 'Bish' was three days earlier than for 'Chandler', while the range in first flowering dates was very similar for both varieties (Table 29).

TABLE 29

| Selection | Date of First Flowering | | Date of First Leaf Emergence | |
|---|---|---|---|---|
| | Mean | Range | Mean | Range |
| 'Chandler' | March 13 | March 7–22 | March 10 | March 7–15 |
| 'Bish' | March 10 | March 5–22 | March 15 | March 10–21 |

Observations were of plants grown in Reidsville, NC in 2003.

First leaf emergence in spring was, on average, five days later than the date of first flowering for 'Bish', while average first leaf emergence was three days earlier than first flowering for 'Chandler'. For 'Bish', infloresence height is generally equal to foliage canopy height.

As observed in May 2004 in Raleigh N.C., the mean fruiting truss length was 21 cm, with a range of (18)19–24 (27) cm. The average number of crowns was 4 (range: 3–5).

Plants and Foliage: Fruiting plants of 'Bish' are generally of equal vigor to 'Chandler'. Mean canopy height was equal for the two varieties, although the range of variation in canopy heights was greater for 'Chandler' (Table 30).

TABLE 30

| Character | | Variety 'Chandler' | Variety 'Bish' |
|---|---|---|---|
| Canopy Height (cm) | Mean | 26 | 26 |
| | Range | 22–30 | 25–27 |
| Mid-tier Leaflet | | | |
| Length (mm) | Mean | 67 | 71 |
| | Range | 55–80 | 60–82 |
| Width (mm) | Mean | 62 | 60 |
| | Range | 55–72 | 55–70 |
| Mid-tier Leaf | | | |
| Length (mm) | Mean | 87 | 84 |
| | Range | 70–105 | 70–100 |
| Width (mm) | Mean | 119 | 136 |
| | Range | 95–166 | 113–160 |
| Leaflets/Leaf | | 3 (rarely 4) | 3 |
| Leaf Convexity | | Mostly Flat-Convex Some Flat | Mainly convex |
| Leaf Serrations | | | |
| Number | | Many | Many |
| Shape | | Semi-Pointed | Semi-Pointed |
| Leaf Pubescence | | Moderate | Moderate |
| Petiole Pubescence | | | |
| Density | | Moderate to Heavy | Heavy |
| Direction | | Acropetal to Perpendicular | Mostly Basipetal |

Observations were of plants grown in Reidsville, NC in 2003.

Figure 3:
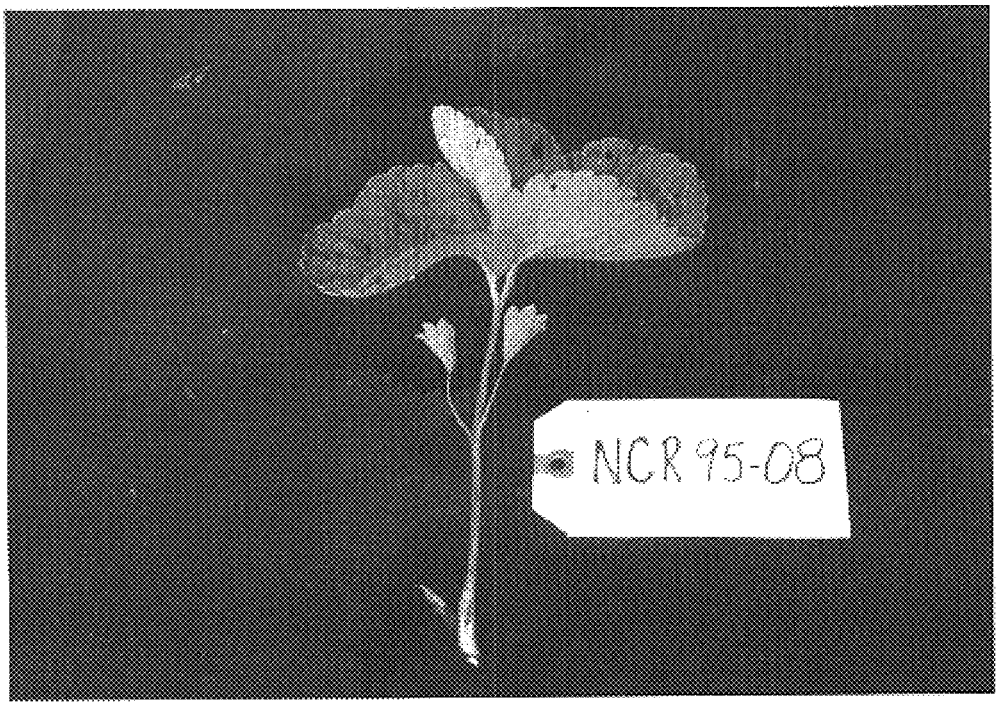
FIG. 3 shows a typical leaf of 'Bish' strawberry.

Individual leaflets of 'Bish' were very similar in size to those of 'Chandler'. Leaflets of 'Bish' tend to be broadly elliptic-ovate, while those of 'Chandler' are generally broadly elliptic. Leaves of 'Bish' are similar in length and somewhat broader than 'Chandler'. 'Bish' leaves are generally convex (FIG. 3) while those of 'Chandler' are mostly flat-convex. Pubescence on leaves of 'Bish' is moderate, while petiole pubescence is heavy and mostly basipetal in direction. 'Bish' leaves generally show a slight puckering between the veins. The color of the adaxial surface of the leaves of 'Bish' matches RHS color chip 137B, and the abaxial surface corresponds to RHS color chip 147C. One notable feature of 'Bish' is the presence of two leafy petiole bracts (FIG. 3). These structures occur consistently on mid-tier leaves. They are typically quite prominent with a mean length of 43 mm and a range of 20–55 mm. Similar petiole bracts also occur on the variety 'Sweet Charlie'. However, 'Sweet Charlie' can be distinguished from 'Bish' by having lighter green and more strongly convex leaves. Petiole bracts only occur occasionally on 'Chandler' and 'Camarosa' and have been observed to be mostly rudimentary when they do occur.

'Bish' is more similar in overall morphological appearance to its 'Delmarvel' parent than to any other current variety. The primary morphological difference between 'Bish' and 'Delmarvel' is the absence of petiole bracts on the latter variety. In addition, 'Delmarvel' is not adapted to annual hill culture, which 'Bish' is.

Disease Resistance: One of the major disadvantages of 'Chandler' and 'Camarosa' varieties in annual hill culture throughout the Southeastern region of the United States is extreme susceptibility to anthracnose fruit rot caused by *Colletotrichum acutatum*. With the industry-wide adoption of these two varieties, anthracnose fruit rot is now the primary disease limiting strawberry production in this region. Field reaction of 'Bish', 'Chandler' and 'Camarosa' to anthracnose fruit rot is presented in Tables 1–14. The extent of anthracnose fruit rot varied widely from year to year and site to site. This variation is due both to the level of inoculum available and weather. Warm, humid and especially rainy weather is highly favorable to disease development. Consistently, 'Bish' was significantly more resistant to anthracnose fruit rot than either 'Chandler' or 'Camarosa'. Throughout the test period, 'Bish' never exceeded 4.8%, by weight, of fruit infected, while both 'Chandler' and 'Camarosa' had up to 50% infection. For annual hill culture strawberries in the Upper South/Middle Atlantic regions, carry-over plantings for a second year is an important consideration, and anthracnose susceptibility has been the main deterrent to this practice. The anthracnose resistance of 'Bish' makes it adaptable to carry-over in these regions. 'Bish' is at least moderately resistant to other fungal leaf diseases which commonly occur in this region including leaf scorch (*Diplocarpon earliana*), leaf blight (*Phomopsis obscurans*) and powdery mildew (*Spaerotheca macularis*).

That which is claimed is:

1. A new and distinct variety of *Fragaria×ananassa* Duch. plant named 'Bish', substantially as described and illustrated herein.

* * * * *